United States Patent [19]

Rivier et al.

[11] Patent Number: 5,043,322

[45] Date of Patent: Aug. 27, 1991

[54] CYCLIC GRF ANALOGS

[75] Inventors: Jean E. F. Rivier; Catherine L. Rivier; Wylie W. Vale, Jr., all of La Jolla, Calif.

[73] Assignee: The Salk Institute for Biological Studies, San Diego, Calif.

[21] Appl. No.: 223,277

[22] Filed: Jul. 22, 1988

[51] Int. Cl.$^5$ ....................... A61K 37/43; C07K 7/10
[52] U.S. Cl. ........................................ 514/12; 530/324
[58] Field of Search ........................... 514/12; 530/324

[56] References Cited

U.S. PATENT DOCUMENTS

| 4,518,586 | 5/1985 | Rivier et al. | 514/12 |
| 4,528,190 | 7/1985 | Vale, Jr. et al. | 514/12 |
| 4,563,352 | 1/1986 | Rivier et al. | 514/12 |
| 4,595,676 | 6/1986 | Spiess et al. | 514/12 |
| 4,626,523 | 12/1986 | Vale, Jr. et al. | 514/12 |
| 4,661,472 | 4/1987 | Rivier et al. | 530/328 |
| 4,689,318 | 8/1987 | Kaiser et al. | 514/12 |
| 4,734,399 | 3/1988 | Felix et al. | 514/12 |
| 4,784,987 | 11/1988 | Rivier et al. | 530/324 |

FOREIGN PATENT DOCUMENTS 0307860  3/1989  European Pat. Off. ............ 530/324

OTHER PUBLICATIONS

Felix et al., "Synthesis and Biological Activity of Novel Linear and Cyclic GRF Analogs," Peptides 1987, pp. 465-467, Ed. by Garland R. Marshall, ESCOM, Leiden, 1988.

Primary Examiner—Lester L. Lee
Assistant Examiner—S. G. Marshall
Attorney, Agent, or Firm—Fitch, Even, Tabin & Flannery

[57] ABSTRACT

Synthetic peptides which stimulate the release of pituitary GH in animals, including humans, and are more resistant to enzymatic degradation in the body than hGRF having the sequence: (B)$R_1$-$R_2$$R_3$-Ala-Ile-Phe-Thr-$R_8$-Ser-$R_{10}$-Arg-$R_{12}$$R_{13}$-Leu-$R_{15}$-Gln-Leu-$R_{18}$-Ala-Arg-$R_{21}$-$R_{22}$-Leu-$R_{24}$-$R_{25}$-Ile-$R_{27}$-$R_{28}$-$R_{29}$-Gln-Gln-Gly-Glu-$R_{34}$-Asn-Gln-Glu-$R_{38}$$R_{39}$-$R_{40}$-Arg-$R_{42}$-$R_{43}$-$R_{44}$ wherein $R_1$ is Tyr, D-Tyr, Met, D-Met, Phe, D-Phe, pCl-Phe, Leu, His or D-His; B is H, $C^\alpha$Me, $N^1$Me, desamino, Ac or For; $R_2$ is Ala, D-Ala, NMA or D-NMA; $R_3$ is Asp or D-Asp; $R_8$ is Ser, Asn, Lys, Arg, Asp or Gln; $R_{10}$ is Tyr, D-Tyr or Phe; $R_{12}$ is Arg or Lys; $R_{13}$ is Ile, Val, Leu or Ala; $R_{15}$ is Gly, Ala or β-Ala; $R_{18}$ is Ser or Tyr; $R_{21}$ is Lys, D-Lys, Arg or D-Arg; $R_{22}$ is Leu, Ile, Ala or Val; $R_{24}$ is Gln or His; $R_{25}$ is cys, abu, asp, glu, orn, lys, dab or dap; $R_{27}$ is Met, D-Met, Ala, Nle, Ile, Leu, Nva or Val; $R_{28}$ is Asn or Ser; $R_{29}$ is cys, abu, asp, glu, orn, lys, dab or dap; $R_{34}$ is Ser or Arg; $R_{38}$ is Arg or Gln; $R_{39}$ is Gly or Arg; $R_{40}$ is Ala or Ser; $R_{42}$ is Phe or Ala; $R_{43}$ is Asn or Arg; $R_{44}$ is a natural amino acid, such as Leu or Val. C-terminal sequences of from 1 to 15 residues beginning at $R_{44}$ and extending as far as up to $R_{29}$ may be deleted. These peptides as well as their nontoxic salts may also be used diagnostically.

20 Claims, No Drawings

CYCLIC GRF ANALOGS

"This invention was made with Government support under Grant No. AM-26741, awarded by the National Institutes of Health. The Government has certain rights in this invention."

The present invention relates to peptides having influence on the function of the pituitary gland in humans and other animals. In particular, the present invention is directed to peptides which promote the release of growth hormone by the pituitary gland.

BACKGROUND OF THE INVENTION

Physiologists have long recognized that the hypothalamus controls the secretory functions of the adenohypophysis with the hypothalamus producing special substances which stimulate or inhibit the secretion of each pituitary hormone. A hypothalamic inhibitory factor was characterized in 1972 in the form of somatostatin which inhibits the secretion of growth hormone(GH). In 1982, human pancreatic releasing factors were isolated from extracts of human pancreatic tumors, purified, characterized, synthesized and tested, which were found to promote the release of GH by the pituitary. Both of these hypophysiotropic factors have been reproduced by total synthesis, and analogs of the native structures have been synthesized. Human hypothalamic GH releasing factor has precisely the same structure; thus, the term hGRF is used hereinafter.

SUMMARY OF THE INVENTION

Synthetic polypeptides have now been synthesized and tested which release GH from cultured pituitary cells, which have increased resistance to enzymatic degradation in the body, and which exhibit very substantially increased potency. It is believed that these advantageous properties result from the peptides having a cyclic form which accounts for increased stability. These peptides preferably have a cyclizing bond between the residues in positions 25 and 29. Preferably, the bond is a disulfide bond between a pair of cysteine residues which may be either D-Cys or L-Cys. Alternatively, the cyclizing bond may be a amide bond between an amino side chain and a carboxyl side chain on these two residues. Ala or β-Ala is preferably substituted in the 15-position, and Nle is preferably present in the 27-position. Lys, Arg, Ser, Glu or Asp may also be substituted in the 8-position. The peptides may also have one of the following residues in the 1-position: Tyr, D-Tyr, Met, D-Met, Phe, D-Phe, pCl-Phe, Leu, His and D-His, which residue may optionally have a methyl substitution either on the alpha-carbon or L(ame) or in the alpha-amino group (Name). The alpha-amino group may also be deleted (desamino); or the alpha-amino group may be acylated, preferably by acetyl (Ac) or formyl (For). The peptides may optionally have D-Ala, NMA or D-NMA at the 2-position and/or D-Asp at the 3-position and/or Arg at the 12-position and/or Phe or D-Tyr at the 10-position. They may also have D-Met or Nva or other residues instead of Met or Nle in the 27-position and/or may have Asn in the 28-position. The residues in the 13- and 22-positions may be any of the following: Leu, Ile, Ala and Val.

Pharmaceutical compositions in accordance with the invention include such analogs which are between about 29 and 44 residues in length, or a nontoxic salt of any of these, dispersed in a pharmaceutically or veterinarily acceptable liquid or solid carrier. Such pharmaceutical compositions can be used in clinical medicine, both human and veterinary, for administration for therapeutic purposes, and also diagnostically. Moreover, they can be used to promote the growth of warm-blooded animals, including fowl, and in aquiculture for cold-blooded animals, e.g. fish, eels, etc.

DETAILED DESCRIPTION OF PREFERRED EMBODIMENTS

The nomenclature used to define the peptides is that specified by Schroder & Lubke, "The Peptides", Academic Press (1965), wherein in accordance with conventional representation the amino group at the N-terminus appears to the left and the carboxyl group at the C-terminus to the right. By natural amino acid is meant one of common, naturally occurring amino acids found in proteins comprising Gly, Ala, Val, Leu, Ile, Ser, Thr, Lys, Arg, Asp, Asn, Glu, Gln, Cys, Met, Phe, Tyr, Pro, Trp and His. By Nle is meant norleucine, and by Nva is meant norvaline. Where the amino acid residue has isomeric forms, it is the L-form of the amino acid that is represented unless otherwise expressly indicated. The lower case version is used to represent that either the D- or the L-isomer may be included, i.e. cys means D-Cys or L-Cys; orn means D-or L-ornithine; dab means D- or L- a, γ diamino butyric acid; dap means D- or L-a,β diamino propionic acid. Reference is respectively made to the L-isomers as either Dab or daB and either Dap or daP, and by a bu is meant a-amino butyric acid. D-NMA signifies the D-isomer of alanine wherein the alpha-amino group is substituted by methyl; NMT likewise signifies N-methyl tyrosine, which is also denoted $N^a$MeTyr.

The invention generally provides synthetic peptides having the following sequence (I):

(B)$R_1$—$R_2$—$R_3$—Ala—Ile—Phe—Thr—$R_8$—Ser—$R_{10}$—

—Arg—$R_{12}$—$R_{13}$—Leu—$R_{15}$—Gln—Leu—$R_{18}$—Ala—

—Arg—$R_{21}$—$R_{22}$—Leu—$R_{24}$—$R_{25}$—Ile—$R_{27}$—$R_{28}$—$R_{29}$—

—Gln—Gln—Gly—$R_{34}$—Asn—Gln—Glu—$R_{38}$—$R_{39}$—

$R_{40}$—Arg—$R_{42}$—$R_{43}$—$R_{44}$ wherein $R_1$ is Tyr, D-Tyr, Met, D-Met, Phe, D-Phe, pCl-Phe, Leu, His or D-His; B is H, $C^a$Me, $N^a$Me, desamino, Ac or For; $R_2$ is Ala, D-Ala, NMA or D-NMA; $R_3$ is Asp or D-Asp; $R_8$ is Ser, Asn, Lys, Arg, Asp or Gln; $R_{10}$ is Tyr, D-Tyr or Phe; $R_{12}$ is Arg or Lys; $R_{13}$ is Ile, Val, Leu or Ala; $R_{15}$ is Gly, Ala or B-Ala; $R_{18}$ is Ser or Tyr; $R_{21}$ is Lys, D-Lys, Arg or D-Arg; $R_{22}$ is Leu, Ile, Ala or Val; $R_{24}$ is Gln or His; $R_{25}$ is cys, abu, asp, glu, orn, lys, dab or dap; $R_{27}$ is Met, D-Met, Ala, Nle, Ile, Leu, Nva or Val; $R_{28}$ is Asn or Ser; $R_{29}$ is cys, abu, asp, glu, orn, lys, dab or dap; $R_{34}$ is Ser or Arg; $R_{38}$ is Arg or Gln; $R_{39}$ is Gly or Arg; $R_{40}$ is Ala or Ser; $R_{42}$ is Phe or Ala; $R_{43}$ is Asn or Arg; $R_{44}$ is a natural amino acid, such as Leu or Val; provided however that any C-terminal sequence of residues beginning at $R_{44}$ and extending as far as up to $R_{29}$ may be deleted. When $R_{25}$ is cys or abu, $R_{29}$ is cys or abu; when $R_{25}$ is asp or glu, then $R_{29}$ is orn, lys, dab or dap and vice versa. The carboxyl moiety of the amino acid residue at the C-terminus may be any of the following radicals:

—COOR, —CRO, —CONHNHR, —CON(R)(R') or —CH$_2$OR, with R and R' being lower alkyl, fluoro lower alkyl or hydrogen; methyl, ethyl and propyl are the preferred lower alkyl groups.

Fragments which extend from the N-terminus through residue-29 have good biological potency in effecting the release of GH by the pituitary, and biologically active fragments of 29 or 32 residues in length which have a C-terminus that is an amide or a substituted amide are most preferred. One group of particularly preferred peptides are those having the formula: (B)R$_1$-R$_2$-R$_3$-Ala-Ile-Phe-Thr-Ser-Ser-Tyr-Arg-Arg-R$_{13}$-Leu-R$_{15}$-Gln-Leu-Tyr-Ala-Arg-R$_{21}$-R$_{22}$-Leu-His-R$_{25}$-Ile-R$_{27}$-Asn-R$_{29}$-NH$_2$ wherein R$_1$ is Tyr, D-Tyr, Met, D-Met, Phe, D-Phe, pCl-Phe, Leu, His or D-His; B is H, C$^a$Me, N$^a$Me, desamino, Ac or For; R$_2$ is Ala, D-Ala, NMA or D-NMA; R$_3$ is Asp or D-Asp; R$_{13}$ is Ile, Val, Leu or Ala; R$_{15}$ is Gly, Ala or β-Ala; R$_{21}$ is Lys, D-Lys, Arg or D-Arg; R$_{22}$ is Leu, Ile, Ala or Val; R$_{25}$ is cys, abu, asp, glu, orn, lys, dab or dap; R$_{27}$ is Met, D-Met, Ala, Nle, Ile, Leu, Nva or Val; and R$_{29}$ is cys, abu, asp, glu, orn, lys, dab or dap. When the peptide has 40 or more residues, there is no clear preference for the moiety at the C-terminus.

The peptides are synthesized by a suitable method, such as by exclusively solid-phase techniques, by partial solid-phase techniques, by fragment condensation or by classical solution couplings. The employment of recently developed recombinant DNA techniques may be used to prepare a portion of an analog containing only natural amino acid residues, which could then be linked to a short N-terminal or C-terminal peptide. For example, techniques of exclusively solid-phase synthesis are set forth in the textbook "Solid-Phase Peptide Synthesis", Stewart & Young, Freeman & Co., San Francisco, 1969, and are exemplified by the disclosure of U.S. Pat. No. 4,105,603, issued Aug. 8, 1978 to Vale et al. Classical solution synthesis is described in detail in the treatise "Methoden der Organischen Chemie (HoubenWeyl): Synthese von Peptiden", E. Wunsch (editor) (1974) Georg Thieme Verlag, Stuttgart, W. Ger. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such chemical syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with side-chain protecting groups linked to the appropriate residues.

Accordingly when such chemical syntheses are used to make the peptides of the present invention, intermediates are produced having the formula (II): (X$^1$)(B)R$_1$(X or X$_2$)-R$_2$-R$_3$(X$^3$)-Ala-Ile-Phe-Thr(X$^4$)-R$_8$(X$^9$)-Ser(X$^4$)-R$_{10}$ (X$_2$)-Arg(X$^6$)-R$^{12}$(X$^6$ or X$^7$)-R$_{13}$-Leu-R$_{15}$-Gln(X$^5$)-Leu-R$_{18}$ (X$^2$)-Ala-Arg(X$^6$)-R$_{21}$(X$^6$ or X$^7$)-R$_{22}$-Leu-R$_{24}$ (X or X$^5$)-R$_{25}$(X$^8$)-Ile-R$_{27}$-R$_{28}$(X$^4$ or X$^5$)-R$_{29}$(X$^8$)-Gln(X$^5$)-Gln(X$^5$)-Gl y-Glu(X$^3$)-R$_{34}$(X$^4$ or X$^6$)-Asn(X$^5$)-Gln(X$^5$)-Glu(X$^3$)-R$_{38}$ (X$^6$ or X$^5$)-R$_{39}$(X$^6$)-R$_{40}$(X$^2$)-Arg(X$^6$)-R$_{42}$-R$_{43}$ (X$^5$ or X$^6$)-R$_{44}$(X$^9$)-X$^{10}$.

X$^1$ is either hydrogen or an a-amino protecting group. The a-amino protecting groups contemplated by X$^1$ are those well known to be useful in the art of stepwise synthesis of polypeptides. Among the classes of a-amino protecting groups which may be employed as X$^1$ are (1) aromatic urethan-type protecting groups, such as fluorenylmethyloxycarbonyl (Fmoc), benzyloxycarbonyl(Z) and substituted Z, such as p-chlorobenzyloxycarbonyl, p-nitrobenzyloxycarbonyl, p-bromobenzyloxycarbonyl, and p-methoxybenzyloxycarbonyl; (2) aliphatic urethan protecting groups, such as t-butyloxycarbonyl (BOC), diisopropylmethyloxycarbonyl, isopropyloxycarbonyl, ethoxycarbonyl, allyloxycarbonyl; and (3) cycloalkyl urethan-type protecting groups, such as cyclopentyloxycarbonyl, adamantyloxycarbonyl, and cyclohexyloxycarbonyl. The preferred a-amino protecting group is BOC, even when an N$^a$Me-substituted residue is employed in the 1-position; of course X$^1$ is H when B is desamino or N$^a$Me.

X is hydrogen or a protecting group for the imidazole nitrogen of His, such as Tos.

X$^2$ may be a suitable protecting group for the phenolic hydroxyl group of Tyr, such as tetrahydropyranyl, tert-butyl, trityl, Bzl, CBZ, 4Br-CBZ and 2,6-dichlorobenzyl(DCB). The preferred protecting group is 2,6-dichlorobenzyl. X$^2$ can be hydrogen which means that there is no side-chain protecting group on the amino acid residue in that position.

X$^3$ is hydrogen or a suitable ester-forming protecting group for the carboxyl group of Asp or Glu, such as benzyl(OBzl), 2,6-dichlorobenzyl, methyl and ethyl.

X$^4$ may be a suitable protecting group for the hydroxyl group of Thr or Ser, such as acetyl, benzoyl, tert-butyl, trityl, tetrahydropyranyl, Bzl, 2,6-dichlorobenzyl and CBZ. The preferred protecting group is Bzl. X$^4$ can be hydrogen, which means there is no protecting group on the hydroxyl group.

X$^5$ is hydrogen or a suitable protecting group for the side chain amido group of Asn or Gln. It is preferably xanthyl(Xan).

X$^6$ is a suitable protecting group for the guanido group of Arg, such as nitro, Tos, CBZ, adamantyloxycarbonyl, and BOC, or is hydrogen.

X$^7$ is hydrogen or a suitable protecting group for the side chain amino group of Lys. Illustrative of suitable side chain amino protecting groups are 2-chlorobenzyloxycarbonyl(2-Cl-Z), Tos, t-amyloxycarbonyl and BOC.

X$^8$ is a protecting group for the sulfhydryl group of Cys, preferably p-methoxybenzyl(MeOBzl), p-methylbenzyl, acetamidomethyl, trityl or Bzl; or a suitable protecting group for an amino side chain which is removable without simultaneously removing the protecting group X$^7$, e.g. a base-labile group such as Fmoc; or a suitable labile protecting group for a carboxyl side chain which is removable without simultaneously removing the protecting group X$^3$, e.g., a base-labile group such as OFm (fluorenylmethyl ester); or is a direct bond between the residues in the 25- and 29-positions when the cyclic form results from a carba or dicarba bond.

X$^9$ is hydrogen or a suitable side-chain protecting group as generally specified above.

Met can optionally be protected by oxygen, but is preferably left unprotected.

The selection of a side chain amino protecting group is not critical except that generally one is chosen which is not removed during deprotection of the a-amino groups during the synthesis. However, for some amino acids, e.g. His, protection is not generally necessary after coupling is completed, and the protecting groups may be the same.

$X^{10}$ is a suitable protecting group for the C-terminal carboxyl group, such as the ester-forming group $X^3$, or is an anchoring bond used in solid-phase synthesis for linking to a solid resin support, or is des-$X^{10}$, in which case the residue at the C-terminal has a carboxyl moiety which is Y, as defined hereinbefore. When a solid resin support is used, it may be any of those known in the art, such as one having the formulae: —O—$CH_2$-resin support, —NH-benzhydrylamine (BHA) resin support or —NH-paramethylbenzhydrylamine (MBHA) resin support. When the unsubstituted amide is desired, use of BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 can be used, or should still other groups than the free acid be desired at the C-terminus, it may be preferable to sythesize the peptide using classical methods as set forth in the Houben-Weyl text.

When B is acetyl, for example, in the final formula, it is possible to employ it as the $X^1$ protecting group for whatever amino acid is used in the 1-position; however, racemization may occur as a result, rendering such protection less desirable. Preferably, a reaction is carried out with the peptide on the resin (after deblocking the a-amino group while the side-chain groups remain protected), e.g. by reacting with acetic acid in the presence of dicyclohexyl carbodiimide (DCC) or preferably with acetic anhydride or by another suitable reaction as known in the art.

In the formula for the intermediate, at least one of the X-groups is a protecting group or $X^{10}$ includes resin support. Thus, the invention also provides a method for manufacturing a peptide of interest by carrying out the following steps: (a) forming a peptide having at least one protective group and the formula (II): wherein: X, $X^1$, $X^2$, $X^3$, $X^4$, $X^5$, $X^6$, $X^7$, $X^8$, and $X^9$ are each either hydrogen or a protective group and $X^{10}$ is either a protective group or an anchoring bond to resin support or is des-$X^{10}$, in which case the residue at the C-terminus may have the desired carboxy moiety; (b) splitting off the protective group or groups or anchoring bond from the peptide of the formula (II); (c) creating a cyclizing bond between $R_{25}$ and $R_{29}$, if not already present either prior to or subsequent to step (b); and (d) if desired, converting the resulting peptide into a nontoxic salt thereof.

In selecting a particular side chain protecting group to be used in the synthesis of the peptides, the following general rules are followed: (a) the protecting group preferably retains its protecting properties and is not be split off under coupling conditions, (b) the protecting group should be stable to the reagent and, with the exception of Xan, is preferably stable under the reaction conditions selected for removing the a-amino protecting group at each step of the synthesis, and (c) the side chain protecting group must be removable, upon the completion of the synthesis containing the desired amino acid sequence, under reaction conditions that will not undesirably alter the peptide chain.

When peptides are not prepared using recombinant DNA technology, they are preferably prepared using solid phase synthesis, such as that generally described by Merrifield, *J. Am. Chem. Soc.*, 85, p 2149 (1963), although other equivalent chemical syntheses known in the art can also be used as previously mentioned. Solid-phase synthesis is commenced from the C-terminus of the peptide by coupling a protected a-amino acid to a suitable resin. Such a starting material can be prepared by attaching an a-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) 38, 1597-98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1-6. BHA and MBHA resin supports are commercially available and are generally used only when the desired polypeptide being synthesized has an unsubstituted amide at the C-terminus.

The C-terminal amino acid, e.g. Asn, protected by BOC and by Xan, can be first coupled to the chloromethylated resin according to the procedure set forth in *Chemistry Letters*, K. Horiki et al. 165-168 (1978), using KF in DMF at about 60° C. for 24 hours with stirring, when for example a 43-residue free acid analog of rat GRF(rGRF) is to be synthesized. Following the coupling of the BOC-protected amino acid to the resin support, the a-amino protecting group is removed, as by using trifluoroacetic acid(TFA) in methylene chloride or TFA alone. The deprotection is carried out at a temperature between about 0° C. and room temperature. Other standard cleaving reagents, such as HCl in dioxane, and conditions for removal of specific a-amino protecting groups may be used as described in Schroder & Lubke, "The Peptides", 1 pp 72-75 (Academic Press 1965).

After removal of the a-amino protecting group, the remaining a-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCC).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke supra, in Chapter III and by Kapoor, *J. Phar. Sci.*, 59, pp 1-27 (1970).

Each protected amino acid or amino acid sequence is introduced into the solid phase reactor in about a fourfold or more excess, and the coupling may be carried out in a medium of dimethylformamide(DMF): $CH_2Cl_2$ (1:1) or in DMF or $CH_2Cl_2$ alone. In cases where incomplete coupling occurs, the coupling procedure is repeated before removal of the a-amino protecting group prior to the coupling of the next amino acid. The success of the coupling reaction at each stage of the synthesis, if performed manually, is preferably monitored by the ninhydrin reaction, as described by E. Kaiser et al., *Anal. Biochem.* 34, 595 (1970). The coupling reactions can be performed automatically, as on a Beckman 990 automatic synthesizer, using a program such as that reported in Rivier et al. *Biopolymers*, 1978, 17, pp 1927-1938.

After the desired amino acid sequence has been completed, cyclization can then be effected or the intermediate peptide can be removed from the resin support by treatment with a reagent, such as liquid hydrogen fluoride, which not only cleaves the peptide from the resin but also cleaves all remaining side chain protecting groups $X$, $X^2$, $X^3$, $X^4$, $X^5$, $X^6$, $X^7$, $X^8$ and $X^9$ and the anchoring bond $X^{10}$ and also the a-amino protecting group $X^1$ if one is used, to obtain the peptide in the form of the free acid. If Met is present in the sequence, the BOC protecting group is preferably first removed using trifluoroacetic acid(TFA)/ethanedithiol prior to cleaving the peptide from the resin with HF to eliminate potential S-alkylation. When using hydrogen fluoride for cleaving, one or more scavengers, such as anisole, cresol, dimethyl sulfide, and methylethyl sulfide are included in the reaction vessel.

Cyclization is preferably effected of the linear peptide, as opposed to cyclizing the peptide while a part of the peptidoresin, when a bond between Cys residues is used. To effect such a disulfide cyclizing linkage, the fully protected peptide can be cleaved from a hydroxymethylated resin or a chloromethylated resin support by ammonolysis, as is well known in the art, to yield the fully protected amide intermediate, which is thereafter suitably cyclized and deprotected; alternatively, deprotection as well as cleavage of the peptide from a benzhydrylamine resin, can take place at 0° C. with hydrofluoric acid (HF). Using some protocols, cyclization may be carried out while the partially protected peptide remains attached to the resin as disclosed in A. M. Felix et al., *Peptides*, Proceedings of the Tenth American Peptide Symposium, May 1987, 465-467 (1988), where an amide cyclizing linkage is used. Such a procedure effectively creates an amide cyclizing bond between the two desired side chains while other residues, such as Asp, Glu and/or Lys, retain their side-chain protection.

The cyclizing step for the GRF peptide analog depends, of course, upon the type of linkage which is desired between the residues in the 25- and 29-positions. When residues of D- or L-Cys are included in both the 25-and 29-positions, it is often more convenient to carry out the cyclizing step following the cleavage from the resin and the removal of all of the protecting groups from the peptide. The cyclic form of the peptide is obtained by oxidizing using a ferricyanide solution, preferably as described in Rivier et al., *Biopolymers*, Vol. 17 (1978), 1927-38, or by air oxidation, or in accordance with other known procedures.

When the cyclization is via an amide bond between a side-chain amino group of the 25-position residue and a side-chain carboxyl group of the 29-position residue (which may be preferred), or vice-versa, it is preferable to synthesize the protected peptide on an MBHA or BHA resin and to derivatize the benzyl ester of the particular carboxyl acid side chain to the hydrazide while the peptide is still attached to the resin and then react it with a selectively deprotected amino-side chain as set forth in U.S. Pat. No. 4,661,472, issued Apr. 28, 1987. Preferably cyclization is accomplished by using a base-labile protecting group, e.g., OFm, for the carboxyl side-chain of the residue to be involved in the amide-bond bridge and using Fmoc as a protecting group for the amino side chain on the other residue that is to be involved. The a-amino protecting group on the 1-position residue, whether or not it is to be acylated, and all of the other side-chain protecting groups remain in place while the two base-labile groups are removed using piperidine or the like. Following this selective removal, the reaction to accomplish cyclization is carried out by treating with BOP which effects substantially complete generation of the amide bond. Following cyclization, the peptide is completely deprotected and cleaved from the resin using a reagent, such as HF. Optionally a BOC-protecting group can be first removed using TFA.

Alternatively, cyclizations of peptides by such amide linkages can also be effected using teachings of U.S. Pat. Nos. 4,115,554, (Sept. 19, 1978); 4,133,805 (Jan. 9, 1979); 4,140,767 (Feb. 20, 1979); 4,161,521 (July 17, 1979); 4,191,754 (March 4, 1980); 4,238,481 (Dec. 9, 1980); 4,244,947 (Jan. 13, 1981); and 4,261,885 (Apr. 14, 1981).

Analogs of GRF including the equivalent of modified cysteine residues in the 25- and 29-positions wherein the disulfide linkage has been replaced by $-CH_2-$ linkage are referred to as dicarba. If only one of the sulfhydryl groups is replaced by a $CH_2$-group, it is referred to as carba, e.g., [carba$^{25}$, Cys$^{29}$]-GRF. Viewed from the aspect of the ultimate peptide, the location which would otherwise have been occupied by a Cys residue instead contains a residue of alpha-amino butyric acid- (aBu). When preparing peptides having such a dicarba or carba-S linkage, the procedure set forth in U.S Pat. No. 4,161,521 is preferably employed (the disclosure of which is incorporated herein by reference) so that, in the intermediate of Formula II, $X^8$ is a direct bond to the other residue.

The following Example I sets forth a preferred method for synthesizing peptides by the solid-phase technique. It will of course be appreciated that the synthesis of a correspondingly longer peptide is effected in the same manner by merely adding the requisite number of amino acids at the C-terminus of the chain. It is presently felt that biologically active fragments should contain the indicated sequence at the N-terminus, and addition of residues to the N-terminus is not considered advantageous.

EXAMPLE I

The synthesis of the peptide [N$^a$MeTyr$^1$, Ala$^{15}$, D-Cys$^{25}$, Nle$^{27}$,Cys$^{29}$]-rGRF(1-29)-NH$_2$ having the formula:

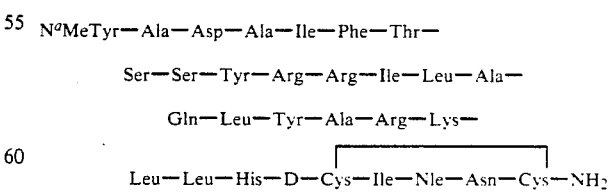

is conducted in a stepwise manner using a Beckman 990 peptide synthesizer on a commercially available MBHA resin as generally described in Vale et al. U.S. Pat. No. 4,292,313. Coupling of BOC-Cys(MeOBzl) to the resin results in the substitution of about 0.35 mmol. Cys per gram of resin.

After deblocking and neutralization, the peptide chain is built step-by-step on the resin. Deblocking, neutralization and addition of each amino acid is performed in general accordance with the procedure set forth in detail in Rivier, J, *J. Amer. Chem. Soc.*, 96, 2986–2992 (1974). All solvents that are used are carefully degassed by sparging with an inert gas, e.g. helium or nitrogen.

Deblocking is preferably carried out in accordance with Schedule A which follows:

SCHEDULE A

| Reagent | Mixing time (Min.) |
| --- | --- |
| 1. 60% TFA/2% ethanedithiol | 10 |
| 2. 60% TFA/2% ethanedithiol | 15 |
| 3. IPA/1% ethanedithiol | 0.5 |
| 4. Et$_3$N (10%) in CH$_2$Cl$_2$ | 0.5 |
| 5. MeOH | 0.5 |
| 6. Et$_3$N (10%) in CH$_2$Cl$_2$ | 0.5 |
| 7. MeOH (twice) | 0.5 |
| 8. CH$_2$Cl$_2$ (twice) | 0.5 |

The couplings are preferably carried out as set out in Schedule B which follows:

SCHEDULE B

| Reagent | Mixing time (Min.) |
| --- | --- |
| 9. DCC | — |
| 10. Boc-amino acid | 50–90 |
| 11. MeOH (twice) | 0.5 |
| 12. CH$_2$Cl$_2$ (twice) | 0.5 |
| 13. Ac$_2$O (3M) in CH$_2$Cl$_2$ | 15.0 |
| 14. CH$_2$Cl$_2$ | 0.5 |
| 15. MeOH | 0.5 |
| 16. CH$_2$Cl$_2$ (twice) | 0.5 |

Briefly, one or two mmol. of BOC-protected amino acid in methylene chloride is used per gram of resin, plus one equivalent of 1.0 molar DCC in methylene chloride for two hours. When BOC-Arg(Tos) is being coupled, a mixture of 50% DMF and methylene chloride is used. Bzl ether is used as the hydroxyl side-chain protecting group for Ser and Thr. The amido group of Asn or Gln is protected by Xan when DCC coupling is used, as is preferred; however, protection may also be omitted. P-nitrophenyl ester(ONp) may also be used to activate the carboxyl end of Asn or Gln, and for example, BOC-Asn(ONp) can be coupled overnight using one equivalent of HOBt in a 50% mixture of DMF and methylene chloride, in which case no DCC is added. 2-chloro-benzyloxycarbonyl(2Cl-Z) is used as the protecting group for the Lys side chain. Tos is used to protect the guanido group of Arg and the imidazole nitrogen of His, and the Asp side-chain carboxyl group is protected with OBzl. MeOBzl is used as a protecting group for the sulfhydryl group of Cys. The phenolic hydroxyl group of Tyr is protected with 2,6-dichlorobenzyl(DCB). At the end of the synthesis, the following composition is obtained: BOC-N$^\alpha$MeTyr(X$_2$)-Ala-Asp(X$^3$)-Ala-Ile-Phe-Thr(X$^4$)-Ser (X$^4$)-Ser(X$^4$)-Tyr(X$_2$)-Arg(X$^6$)-Arg(X$^6$)-Ile-Leu-Ala-Gln (X$^5$)-Leu-Tyr(X$_2$)-Ala-Arg(X$^6$)-Lys(X$^7$)-Leu-Leu-His (X)-D-Cys -Ile-Nle-Asn(X$^5$)-Cys(X$^8$)-X$^{10}$ wherein X is Tos, X$^2$ is DCB, X$^3$ is OBzl, X$^4$ is Bzl, X$^5$ is Xan, X$^6$ is Tos, X$^7$ is 2Cl-Z, X$^8$ is MeOBzl and X$^{10}$ is NH-MBHA-resin support. Xan may have been partially or totally removed by TFA treatment used to deblock the a-amino protecting group.

In order to cleave and deprotect the protected peptide-resin, it is treated with 1.5 ml. anisole, 0.5 ml. methylethylsulfide and 15 ml. hydrogen fluoride(HF) per gram of peptide-resin, at −20° C. for one-half hour and at 0° C. for one-half hour. After elimination of the HF under high vacuum, the resin-peptide remainder is washed alternately with dry diethyl ether and chloroform, and the peptide is then extracted with degassed 2N aqueous acetic acid and separated from the resin by filtration.

The peptide is then air-oxidized for about 48 hours at about 4° C. and then for about 3 more days at room temperature (or until complete disappearance of —SH as measured by the Ellman test—see *Archives Biochem. Biophys.* 82, 1959, p. 70) to create a disulfide linkage between the cysteine residues in each molecule.

The cleaved, deprotected and cyclic peptide is then dissolved in 0–5% acetic acid and subjected to purification which may include Sephadex G-50 fine gel filtration.

The peptide is then further purified by preparative or semi-preparative HPLC as described in Rivier et al., *J. of Chromatography*, 288, 303–328 (1984); Rivier et al., *Peptides: Structure and Biological Function*, (1979) pp 125–8; and Marki et al. *J. Am. Chem. Soc.* 103, 3178 (1981). Cartridges fitting Waters Associates prep LC-500 are packed with 15–20 μ C$_{18}$ Silica from Vydac (300A). A gradient of CH$_3$CN in TEAP is generated by a low pressure Eldex gradient maker, as described in Rivier, J., *J. Liq. Chromatography* 1, 343–367 (1978). The chromatographic fractions are carefully monitored by HPLC, and only the fractions showing substantial purity are pooled. Desalting of the purified fractions, independently checked for purity, is achieved using a gradient of CH$_3$CN in 0.1% TFA. The center cut is then lyophilized to yield the desired peptide, the purity of which can be greater than 98%.

The peptide is judged to be homogeneous using thin layer chromatography and several different solvent systems. It is specifically subjected to reversed-phase high pressure liquid chromatography using the Waters HPLC system described above with a 0.21×15 cm column packed with 5 μm C$_{18}$ silica, 300A pore size; the buffers used were an aqueous triethylammonium phosphate solution at pH 3.0 consisting of 1.0 ml. of H$_3$PO$_4$ and 1.6 ml. of triethylamine per 1000 ml. of solution, plus acetonitrile. The determination was run at room temperature. Buffer A included 5% CH$_3$CN, whereas buffer B included 75% CH$_3$CN. The flow rate was 0.6 ml. per minute, beginning with 20% buffer B and proportionately increasing over 60 minutes to reach 95% buffer B. The retention time was 34.45 minutes.

Amino acid analysis of the resultant, purified peptide is consistent with the formula for the prepared structure, showing the following values for each amino acid in the chain: Asp(2.13), Thr(1.00), Ser(1.75), Glu(1.06), Cys(1.83), Ala(4.00), CH$_3$Tyr(1.17), Ile(2.71), Leu(4.33), Nle(1.28), Tyr(2.14), Phe(0.94), Lys(1.00), His(1.04) and Arg(3.20). The optical rotation is measured on a photoelectric polarimeter as $[\alpha]^{22}{}_D = -62.9° \pm 1 (c=1, 1\%$ acetic acid).

EXAMPLE IA

The synthesis of Example I is repeated substituting L-Cys for D-Cys in the 25-position and substituting D-Cys for L-Cys in the 29-position to synthesize the amidated peptide having the formula:

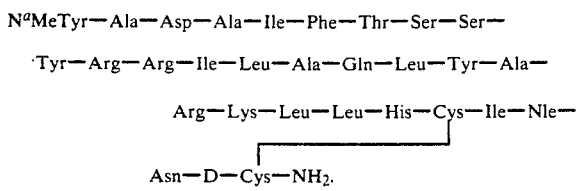

The peptide is judged to be homogeneous using thin layer chromatography and several different solvent systems. It is specifically subjected to reversed-phase high pressure liquid chromatography using the Waters HPLC system described above with a 0.21×15 cm column packed with 5 μm $C_{18}$ silica, 300A pore size; the buffers used were an aqueous 0.1% trifluoroacetic acid solution consisting of 1.0 ml. of TFA per 1000 ml. of solution, plus acetonitrile. The determination was run at 37° C. Buffer A included 5% $CH_3CN$, whereas buffer B included 80% $CH_3CN$. The flow rate was 1.0 ml. per minute, beginning with 10% buffer B and proportionately increasing over 30 minutes to reach 95% buffer B. The retention time was 20.68 minutes.

Amino acid analysis of the resultant, purified peptide is consistent with the formula for the prepared structure, showing substantially integer-values for each amino acid in the chain. The optical rotation is measured on a photoelectric polarimeter as $[\alpha]^{22}_D = -79.2° \pm 1(c=1, 1\%$ acetic acid).

EXAMPLE II

The synthesis the 44-residue amidated peptide c(25-29)[$N^\alpha$MeTyr$^1$, D-NMA$^2$, Ala$^{15}$, Nle$^{27}$, daP$^{29}$]-hGRF(1-44)-NH$_2$ having the formula:

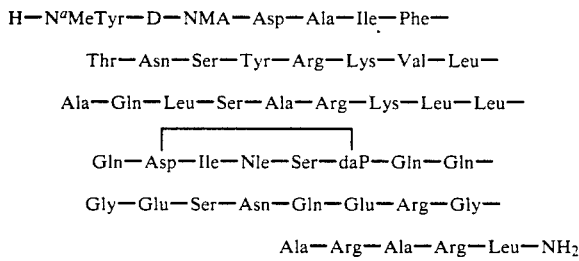

is conducted in a stepwise manner using a Beckman 990 Peptide Synthesizer on an MBHA resin as generally described in Example I to assemble the intermediate having the formula: BOC-$N^\alpha$MeTyr(X$_2$)-Ala-Asp(X$^3$)-Ala-Ile-Phe-Thr (X$^4$)-Asn(X$^5$)-Ser(X$^4$)-Tyr(X$_2$)-Arg(X$^6$)-Lys(X$^7$)-Val-Leu-Ala-Gln (X$^5$)-Leu-Ser(X$^4$)-Ala-Arg(X$^6$)-Lys(X$^7$)-Leu-Leu-Gln (X$^5$)-Asp(OFm)-Ile-Nle-Ser(X$^4$)-daP(Fmoc)-Gln (X$^5$)-Gln(X$^5$)-Gly-Glu(X$^3$)-Ser(X$^4$)-Asn(X$^5$)-Gln(X$^5$)-Glu (X$^3$)-Arg(X$^6$)-Gly-Ala-Arg(X$^6$)-Ala-Arg(X$^6$)-Leu-NH-MBHA resin support, wherein X$^2$-X$^7$ are as specified in Example. The selective deprotection and cyclization are carried out as follows.

4 g. of protected-peptidyl resin (containing about 5 meq. of peptide), 2.20 g. (5 meq.) BOP [Benzotriazolyl-N-oxytris(dimethylamino)phosphonium hexafluorophosphate] and 10 meq. of diisopropylethylamine are suspended and stirred for 2 hours at room temperature. The peptidoresin is filtered, washed with DMF, MeOH, $CH_2Cl_2$ and MeOH, and finally dried.

4 g. of the protected peptidoresin is treated with 60% TFA in $CH_2Cl_2$ to remove the BOC-protecting group and then with 10-15 ml of distilled HF, in the presence of 1.5 ml of anisole as a scavenger, at 0° C. for 60 minutes to remove the remaining protecting groups and cleave the peptide from the resin. HF is removed under high vacuum, and the peptide is precipitated with anhydrous ethyl ether. The solid is collected, dissolved in 50 ml $CH_3CN:H_2O$ (1:1) and lyophilized. It is then purified using RP-HPLC, as described with respect to Example No. 1. The peptide is judged to be substantially pure using TLC and HPLC.

EXAMPLE III

The synthesis of c(25-29) [D-NMA$^2$, D-Glu$^{25}$, Nle$^{27}$, Orn$^{29}$]-rGRF(1-43)—OH having the formula:

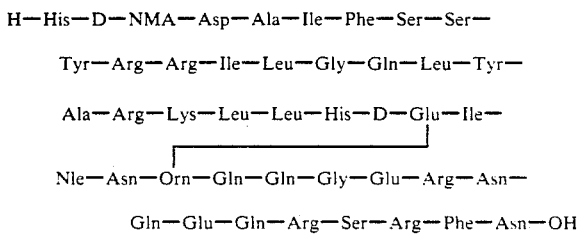

is conducted in a stepwise manner using a Beckman 990 Peptide Synthesizer using a chloromethylated resin, with initial coupling as described in *Chemistry Letters, supra*, and thereafter in the manner generally described in Example II. The peptide is judged to be substantially pure using TLC and HPLC.

EXAMPLE IV

The synthesis of the hGRF analog fragment, [$N^\alpha$MeTyr$^1$, Lys$^8$, Ala$^{15}$, Nle$^{27}$, Asn$^{28}$, Cys$^{29}$]-hGRF(1-29)-NHEt having the formula:

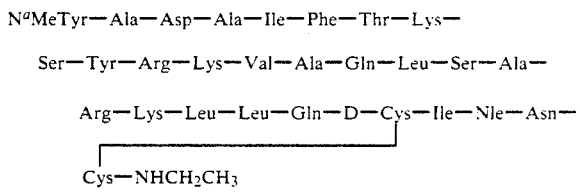

is conducted in a stepwise manner using a Beckman 990 Peptide Synthesizer on an resin as described in U.S. Pat. No. 4,569,967. The linear peptide is removed from the resin by treatment with HF and cyclization and purification are carried out as set forth in Example I. This analog is judged to be substantially pure using TLC and HPLC.

EXAMPLE V

Analogs of rGRF as indicated in TABLE I having the formula:

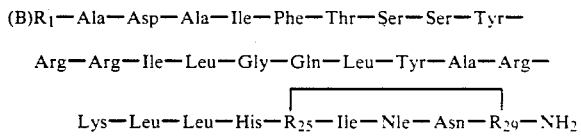

are prepared by the solid-phase procedure referred to above.

TABLE I

| B | R$_1$ | R$_{25}$ | R$_{29}$ |
|---|---|---|---|
| 5 | Ac | His | Cys | aBu |

TABLE I-continued

|  | B | $R_1$ | $R_{25}$ | $R_{29}$ |
|---|---|---|---|---|
| 6 | " | D-Phe | aBu | D-aBu |
| 7 | For | Tyr | Asp | daP |
| 8 | " | D-Tyr | " | D-daB |
| 9 | C$^a$Me | Phe | daP | D-Asp |
| 10 | " | Met | " | Glu |
| 11 | " | D-Met | Orn | " |
| 12 | Ac | Leu | daB | D-Asp |
| 13 | N$^a$Me | pCl-Phe | Cys | D-Cys |
| 14 | Ac | D-His | Orn | Asp |
| 15 | " | D-Tyr | daP | " |
| 16 | desamino | His | " | D-Glu |
| 17 | " | Phe | Glu | daP |

Peptides such as Nos. 5 and 6 are synthesized by employing the general teaching of U.S. Pat. No. 4,161,521.

EXAMPLE VI

Analogs of hGRF as indicated in TABLE II having the formula:

H—Tyr—Ala—Asp—Ala—Ile—Phe—Thr—$R_8$—Ser—Tyr—

Arg—Lys—$R_{13}$—Leu—Gly—Gln—Leu—Ser—Ala—Arg—

Lys—Leu—Leu—Gln—$R_{25}$—Ile—Nle—Ser—$R_{29}$—NH$_2$ are prepared by the solid-phase procedure referred to above.

TABLE II

|  | $R_8$ | $R_{13}$ | $R_{25}$ | $R_{29}$ |
|---|---|---|---|---|
| 18 | Gln | Ala | daP | Asp |
| 19 | " | Ile | Orn | " |
| 20 | Lys | " | daB | Glu |
| 21 | " | Val | D-Lys | Asp |
| 22 | " | Leu | daP | " |
| 23 | Asn | " | " | D-Glu |
| 24 | " | Ala | daB | " |
| 25 | " | Ile | " | Asp |
| 26 | Ser | " | Lys | " |
| 27 | " | Val | D-Asp | D-daP |
| 28 | Arg | " | Asp | D-daB |
| 29 | " | Leu | Glu | " |
| 30 | Asp | " | aBu | D-Cys |
| 31 | " | Ala | Cys | D-aBu |

EXAMPLE VII

Analogs of rGRF as indicated in TABLE III having the formula:

N$^a$MeTyr—Ala—Asp—Ala—Ile—Phe—Thr—Ser—Ser—

Tyr—Arg—Arg—Ile—Leu—Gly—Gln—Leu—Tyr—Ala—

Arg—$R_{24}$—$R_{25}$—Ile—Met—Asn—$R_{29}$—NH$_2$ are prepared by the solid-phase procedure referred to above.

TABLE III

|  | $R_{21}$ | $R_{24}$ | $R_{25}$ | $R_{29}$ |
|---|---|---|---|---|
| 32 | Lys | His | D-Asp | daP |
| 33 | " | " | Cys | Cys |
| 34 | D-Lys | " | " | " |
| 35 | " | Gln | daP | D-Asp |
| 36 | " | " | Orn | Asp |
| 37 | " | His | Asp | daP |
| 38 | Arg | " | " | Lys |

TABLE III-continued

|  | $R_{21}$ | $R_{24}$ | $R_{25}$ | $R_{29}$ |
|---|---|---|---|---|
| 39 | " | " | Glu | D-Lys |
| 40 | D-Arg | " | " | daP |
| 41 | " | " | daB | Asp |
| 42 | Arg | Gln | " | " |
| 43 | Lys | His | D-daB | Glu |
| 44 | " | " | " | D-Glu |
| 45 | D-Lys | " | daP | " |
| 46 | D-Arg | " | " | Asp |
| 47 | " | Gln | Cys | Cys |

EXAMPLE VIII

Analogs of hGRF as indicated in TABLE IV having the formula:

N$^a$MeTyr—$R_2$—Asp—Ala—Ile—Phe—Thr—Asn—Ser—Tyr—

Arg—Lys—Val—Leu—Gly—Gln—Leu—Ser—Ala—Arg—

Lys—Leu—Leu—Gln—$R_{25}$—Ile—$R_{27}$—Ser—$R_{29}$—Gln—

Gln—Gly—Glu—$R_{34}$—Asn—Gln—Glu—Arg—Gly—Ala—

Arg—Ala—Arg—Leu—NH$_2$ are prepared by the solid-phase procedure referred to above.

TABLE IV

|  | $R_2$ | $R_{25}$ | $R_{27}$ | $R_{29}$ | $R_{34}$ |
|---|---|---|---|---|---|
| 48 | D-Ala | D-Cys | Nle | Cys | Ser |
| 49 | " | Asp | Met | daB | " |
| 50 | " | " | D-Met | D-daP | " |
| 51 | " | " | Ala | Orn | " |
| 52 | Ala | D-Asp | Nle | " | Arg |
| 53 | " | D-Glu | Ile | D-Orn | " |
| 54 | " | " | Nle | daB | Ser |
| 55 | " | " | Val | Lys | " |
| 56 | NMA | D-Glu | Leu | daP | " |
| 57 | D-NMA | Glu | Nva | " | " |
| 58 | " | " | " | D-daP | " |
| 59 | " | " | Ala | D-Lys | Arg |

EXAMPLE IX

Analogs of rGRF as indicated in TABLE V having the formula:

H—His—Ala—$R_3$—Ala—Ile—Phe—Thr—Ser—Ser—Tyr—

Arg—Arg—Ile—Leu—Gly—Gln—Leu—Tyr—Ala—Arg—

Lys—Leu—Leu—His—$R_{25}$—Ile—Nle—Ser—$R_{29}$—Gln—

Gln—Gly—Glu—Arg—Asn—Gln—Glu—Gln—Arg—Ser

—Arg—Phe—Asn—$R_{44}$—Y are prepared by the solid-phase procedure referred to above.

TABLE V

|  | $R_3$ | $R_{25}$ | $R_{29}$ | $R_{44}$—Y |
|---|---|---|---|---|
| 60 | Asp | Cys | Cys | NH$_2$ |
| 61 | " | " | aBu | Val—NH$_2$ |
| 62 | D-Asp | " | Cys | Leu—NH$_2$ |
| 63 | " | " | " | OH |
| 64 | " | " | aBu | NHCH$_2$CH$_3$ |
| 65 | Asp | " | " | OH(acetate salt) |
| 66 | " | aBu | D-Cys | NHCH$_3$ |
| 67 | " | " | aBu | Ala—NH$_2$ |

TABLE V-continued

|    | R₃     | R₂₅  | R₂₉    | R₄₄—Y                |
|----|--------|------|--------|----------------------|
| 68 | "      | Glu  | D-daB  | N(CH₃)₂              |
| 69 | D-Asp  | "    | Orn    | NHNH₂                |
| 70 | "      | Asp  | daB    | OCH₃                 |
| 71 | "      | "    | D-daP  | —CH₂OH               |
| 72 | "      | Cys  | Cys    | CHO                  |
| 73 | "      | "    | D-aBu  | NHCFH₂               |
| 74 | Asp    | "    | Cys    | NHCF₂CH₃             |
| 75 | "      | Asp  | D-daB  | OH                   |

EXAMPLE X

Analogs of hGRF as indicated in TABLE VI having the formula:

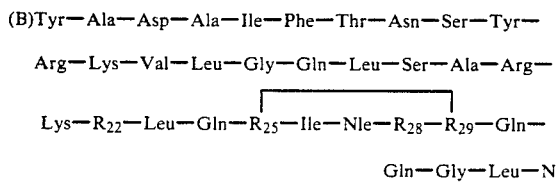

are prepared by the solid-phase procedure referred to above.

TABLE VI

|    | B       | R₂₂  | R₂₅    | R₂₈  | R₂₉    |
|----|---------|------|--------|------|--------|
| 76 | Ac      | Leu  | Asp    | Asn  | D-daP  |
| 77 | Ac      | "    | daP    | "    | Asp    |
| 78 | Ac      | Ala  | D-Cys  | Ser  | Cys    |
| 79 | Ac      | "    | Glu    | "    | D-Orn  |
| 80 | H       | Val  | daP    | "    | Asp    |
| 81 | desamino| "    | "      | Asn  | D-Glu  |
| 82 | "       | Ile  | Lys    | "    | "      |
| 83 | For     | "    | D-daP  | "    | D-Asp  |
| 84 | "       | "    | Cys    | "    | aBu    |
| 85 | NᵃMe    | Leu  | "      | Ser  | D-Cys  |
| 86 | "       | "    | daB    | "    | Asp    |
| 87 | H       | Ala  | "      | Asn  | Glu    |

EXAMPLE XI

Analogs of rGRF as indicated in TABLE VII having the formula:

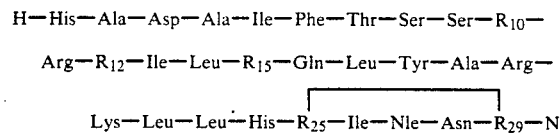

are prepared by the solid-phase procedure referred to above.

TABLE VII

|     | R₁₀    | R₁₂  | R₁₅    | R₂₅    | R₂₉    |
|-----|--------|------|--------|--------|--------|
| 88  | D-Tyr  | Arg  | Ala    | Orn    | D-Glu  |
| 89  | "      | "    | "      | D-Orn  | Asp    |
| 90  | "      | "    | "      | daP    | "      |
| 91  | "      | "    | β-Ala  | "      | Glu    |
| 92  | Tyr    | Lys  | "      | D-daP  | Asp    |
| 93  | "      | "    | Gly    | D-Lys  | "      |
| 94  | "      | "    | "      | Glu    | D-daP  |
| 95  | Phe    | "    | Ala    | "      | daB    |
| 96  | "      | Arg  | "      | aBu    | D-Cys  |
| 97  | "      | "    | Gly    | "      | D-aBu  |
| 98  | D-Tyr  | "    | "      | D-aBu  | Cys    |
| 99  | "      | "    | β-Ala  | D-Orn  | Glu    |
| 100 | "      | "    | Ala    | D-Lys  | D-Asp  |

EXAMPLE XII

Analogs of hGRF as indicated in TABLE VIII having the formula:

H—Tyr—Ala—Asp—Ala—Ile—Phe—Thr—Asn—Ser—Tyr—

Arg—Lys—R₁₃—Leu—Gly—Gln—Leu—Ser—Ala—Arg—

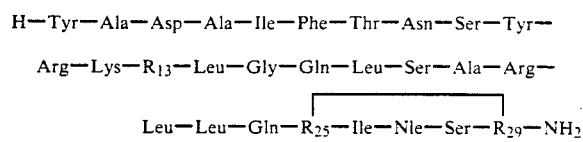

are prepared by the solid-phase procedure referred to above.

TABLE VIII

|     | R₁₃  | R₂₁    | R₂₅    | R₂₉    |
|-----|------|--------|--------|--------|
| 101 | Val  | D-Lys  | Cys    | Cys    |
| 102 | "    | "      | "      | aBu    |
| 103 | "    | "      | aBu    | D-Cys  |
| 104 | Ile  | "      | "      | D-aBu  |
| 105 | "    | Lys    | "      | Cys    |
| 106 | "    | "      | daP    | Glu    |
| 107 | Ala  | "      | D-daB  | "      |
| 108 | "    | "      | daP    | D-Glu  |
| 109 | "    | "      | D-Orn  | "      |
| 110 | Ile  | "      | Asp    | daP    |
| 111 | "    | D-Arg  | Glu    | Lys    |
| 112 | "    | "      | "      | D-daP  |
| 113 | Leu  | "      | D-Glu  | Lys    |
| 114 | "    | Arg    | "      | D-Orn  |
| 115 | "    | "      | Asp    | D-Lys  |
| 116 | Val  | "      | "      | daB    |
| 117 | "    | D-Lys  | "      | D-daP  |
| 118 | Ile  | "      | D-Asp  | daP    |
| 119 | "    | "      | Cys    | aBu    |
| 120 | "    | Lys    | "      | D-Cys  |
| 121 | "    | "      | daP    | Asp    |
| 122 | Ala  | Arg    | "      | "      |

The synthetic peptides prepared in the Examples are compared with synthetic hGRF(1-40)—OH in in vitro assays and are found to exhibit generally greater potencies for the secretion of GH and similar intrinsic activities. All of these synthetic peptides are considered to be biologically active and potentially useful for stimulating the release of GH by the pituitary.

To determine the relative effectiveness of certain representative synthetic peptides to promote the release of growth hormone, in vitro assays are carried out using synthetic hGRF(1-40)—OH as a standard in side-by-side comparison with equimolar concentrations of the representative analogs which have been synthesized. Cultures are used which include cells of rat pituitary glands removed some three to five days previously. Such cultures are considered optimal for the secretion of growth hormone and are used for the comparative testing, in the general manner described in Vale et al. *Endocrinology*, 91, 562-572 (1972) and as more particularly described in Vale et al. *Endocrinology*, 112, 553-1555 (1983). Incubation with the substance to be tested is carried out for 3 to 4 hours, and aliquots of the culture medium are removed and processed to measure their contents in immunoreactive GH(ir GH) by a well-characterized radioimmunoassay.

For example, the results of this comparative testing for equimolar concentrations show that [NᵃMeTyr¹,Ala¹⁵,Cys²⁵,Nle²⁷,D-Cys²⁹]- rGRF(1-29)-NH₂ exhibits a biological potency equal to about twice the biological potency of hGRF(1-40)—OH.

In addition to the in vitro tests for secretion of growth hormone, in vivo experiments inject the synthetic peptides intravenously into urethane-anesthetized male rats and determine that they trigger GH secretion. Blood samples are taken immediately prior to, and 10, 45 and 90 minutes after injections, and GH levels in blood are measured by radioimmunoassay. This in vivo testing of these synthetic peptides shows that they exhibit substantially greater biological potency than that exhibited by hGRF(1-40)—OH; a dosage of 1 μg of the peptide of Example I and a dosage of 5 μg of the peptide of Example IA both invoke an in vivo response at 10 minutes greater than a 25 μg dose of hGRF(1-40)—OH. Moreover, these synthetic cyclic GRF analogs have longer duration of effectiveness, as shown in blood levels of pituitary GH when measured at 45 min. after IV injection for comparable dosages of hGRF(1-40)—OH and the cyclic peptides of the invention. Dosages between about 400 nanograms and about 50 micrograms of these cyclic peptides per Kg. of body weight are considered to be effective in causing GH secretion.

Such synthetic hGRF analogs and rGRF analogs should be useful for human applications in which a physician wishes to elevate GH production. Stimulation of GH secretion by such analogs is of interest in patients with complete or relative GH deficiency caused by underproduction of endogenous GRF. Furthermore, it is probable that increased GH secretion and its attendant increase in growth could be obtained in humans or animals with normal GH levels. Moreover, administration should alter body fat content and modify other GH-dependent metabolic, immunologic and developmental processes. For example, these analogs may be useful as a means of stimulating anabolic processes in human beings under circumstances such as following the incurring of burns. As another example, these analogs may be administered to commercial warm-blooded animals, such as chickens, turkeys, pigs, goats, cattle and sheep, and may be used in aquiculture for raising fish and other cold-blooded marine animals, e.g. sea turtles and eels, and amphibians, to accelerate growth and increase the ratio of protein to fat gained by administering effective amounts of the peptides.

For administration to humans, these synthetic peptides should have a purity of at least about 93% and preferably at least 98%. Purity, for purposes of this application, refers to the intended peptide constituting the stated weight % of all peptides and peptide fragments present. For the administration of such synthetic peptides to commercial and other animals in order to promote growth and reduce fat content, a purity as low as about 5%, or even as low as 0.01%, may be acceptable.

These synthetic peptides or the nontoxic salts thereof, combined with a pharmaceutically or veterinarily acceptable carrier to form a pharmaceutical composition, may be administered to animals, including humans, either intravenously, subcutaneously, intramuscularly, percutaneously, e.g. intranasally or even orally. The administration may be employed by a physician to stimulate the release of GH where the host being treated requires such therapeutic treatment. The required dosage will vary with the particular condition being treated, with the severity of the condition and with the duration of desired treatment.

Such peptides are often administered in the form of nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be orally administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered to humans under the guidance of a physician, and pharmaceutical compositions will usually contain the peptide in conjunction with a conventional, solid or liquid, pharmaceutically-acceptable carrier. Usually, the parenteral dosage will be from about 0.01 to about 1 microgram of the peptide per kilogram of the body weight of the host.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, modifications in the peptide chain, particularly deletions beginning at the carboxyl terminus of the peptide and extending to about position-29, can be made in accordance with the known experimental practices to date to create peptides or peptide fragments that retain all or very substantial portions of the biological potency of the peptide, and such peptides are considered as being within the scope of the invention. Moreover, additions may be made to either terminus, or to both terminals, and/or generally equivalent residues can be substituted for naturally occurring residues, as is well-known in the overall art of peptide chemistry, to produce other analogs having at least a substantial portion of the potency of the claimed polypeptide without deviating from the scope of the invention. Moreover, modifications may be made to the preferred —NH$_2$ group at the C-terminus in accordance with the state of this art today; for example, the usual carboxyl moiety of the amino acid residue at the C-terminus can have the form of the radical —COOR,—CRO,—CONHNHR,—CON(R)(R') or —CH$_2$OR, with R and R' being lower alkyl, fluoro lower alkyl or hydrogen, without deviating from the invention for such modifications result in equivalent synthetic peptides.

Various features of the invention are emphasized in the claims which follow.

What is claimed is:

1. A cyclic synthetic peptide, or a nontoxic salt thereof, having the sequence:

(B)$R_1$—$R_2$—$R_3$—Ala—Ile—Phe—Thr—$R_8$—Ser—$R_{10}$—

—Arg—$R_{12}$—$R_{13}$—Leu—$R_{15}$—Gln—Leu—$R_{18}$—Ala—

—Arg—$R_{21}$—$R_{22}$—Leu—$R_{24}$—$R_{25}$—Ile—$R_{27}$—$R_{28}$—$R_{29}$—

—Gln—Gln—Gly—$R_{34}$—Asn—Gln—Glu—$R_{38}$—$R_{39}$—

$R_{40}$—Arg—$R_{42}$—$R_{43}$—$R_{44}$ wherein $R_1$ is Tyr, D-Tyr, Met, D-Met, Phe, D-Phe, pCl-Phe, Leu, His or D-His; B is H, $C^aMe$, $N^aMe$, desamino, acetyl or formyl; $R_2$ is Ala, D-Ala, NMA or D-NMA; $R_3$ is Asp or D-Asp; $R_8$ is Ser, Asn, Lys, Arg, Asp or Gln; $R_{10}$ is Tyr, D-Tyr or Phe; $R_{12}$ is Arg or Lys; $R_{13}$ is Ile, Val, Leu or Ala; $R_{15}$ is Gly, Ala or β-Ala; $R_{18}$ is Ser or Tyr; $R_{21}$ is Lys, D-Lys, Arg or D-Arg; $R_{22}$ is Leu, Ile, Ala or Val; $R_{24}$ is Gln or His; $R_{25}$ is a D- or L-isomer of Cys, Abu, Asp, Glu, Orn, Lys, Dab or Dap; $R_{27}$ is Met, D-Met, Ala, Nle, Ile, Leu, Nva or Val; $R_{28}$ is Asn or Ser; $R_{29}$ is a D- or L-isomer of Cys, Abu, Asp, Glu, Orn, Lys, Dab or Dap; $R_{34}$ is Ser or Arg; $R_{38}$ is Arg or Gln; $R_{39}$ is Gly or Arg; $R_{40}$ is Ala or Ser; $R_{42}$ is Phe or Ala; $R_{43}$ is Asn or Arg; $R_{44}$ is a natural amino acid; provided however that any C-terminal sequence of residues beginning at $R_{44}$ and extending as far as up to $R_{29}$ may be deleted.

2. The peptide of claim 1 wherein $(B)R_1$ is $N^aMeTyr$.

3. The peptide of claim 1 wherein $R_{25}$ is D-Cys.

4. The peptide of claim 3 wherein $R_{29}$ is Cys.

5. The peptide of claim 1 wherein $R_{22}$ is Ala.

6. The peptide of claim 1 wherein $R_{27}$ is Nle.

7. The peptide of claim 1 wherein $R_{15}$ is Ala.

8. The peptide of claim 1 wherein $R_{28}$ is Asn.

9. The peptide of claim 1 wherein $R_{25}$ is Asp.

10. The peptide of claim 9 wherein $R_{29}$ is

11. The peptide of claim 1 wherein $R_{25}$ is D-Glu and $R_{29}$ is Dap.

12. The peptide of claim 1 wherein $R_{25}$ is Cys and $R_{29}$ is D-Cys.

13. The peptide of claim 1 having the formula c(25-29) [$N^aMeTyr^1$, $Ala^{15}$, $D-Cys^{25}$, $Nle^{27}$, $Cys^{29}$]-rGRF(1-29)-$NH_2$.

14. The peptide of claim 1 having the formula c(25-29) [$N^aMeTyr^1$, $Lys^8$, $Ala^{15}$, $D-Cys^{25}$, $Nle^{27}$, $Asn^{28}$, $Cys^{29}$]-hGRF(1-29)-$NHCH_2CH_3$.

15. The peptide of claim 1 having the formula (25-29) [$N^aMeTyr^1$, $D-Asp^{25}$, $k DaP^{29}$]-rGRF(1-29)-$NH_2$.

16. The peptide of claim 1 having the formula c(25-29) [$N^aMeTyr^1$, $Ala^{15}$, $Cys^{25}$, $Nle^{27}$, $D-Cys^{29}$]-rGRF(1-29)-$NH_2$.

17. The peptide of claim 1 wherein $R_{25}$ is D-Cys, $R_{27}$ is Nle, $R_{29}$ is Cys and residues 30 through 44 are deleted.

18. A pharmaceutical composition for stimulating the release of GH in an animal comprising a peptide of claim 1 or a nontoxic salt thereof, and a pharmaceutically or veterinarily acceptable liquid or solid carrier therefor.

19. A method for the therapeutic treatment to increase secretion of growth hormone of humans which comprises administering an effective amount of a composition in accordance with claim 18.

20. A cyclic synthetic peptide, or a nontoxic salt thereof, having the formula:

$(B)R_1$—$R_2$—$R_3$—Ala—Ile—Phe—Thr—Ser—Ser—Tyr—

Arg—Arg—$R_{13}$—Leu—$R_{15}$—Gln—Leu—Tyr—Ala—Arg—

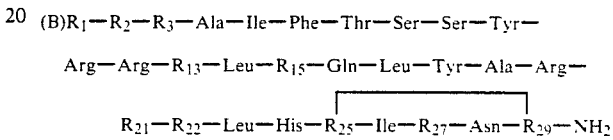

$R_{21}$—$R_{22}$—Leu—His—$R_{25}$—Ile—$R_{27}$—Asn—$R_{29}$—$NH_2$ wherein $R_1$ is Tyr, D-Tyr, Met, D-Met, Phe, D-Phe, pCl-Phe, Leu, His or D-His; B is H, $C^aMe$, $N^aMe$, desamino, acetyl or formyl; $R_2$ is Ala, D-Ala, NMA or D-NMA; $R_3$ is Asp or D-Asp; $R_{13}$ is Ile, Val, Leu or Ala; $R_{15}$ is Gly, Ala or β-Ala; $R_{21}$ is Lys, D-Lys, Arg or D-Arg; $R_{22}$ is Leu, Ile, Ala or Val; $R_{25}$ is a D- or L-isomer of Cys, Abu, Asp, Glu, Orn, Lys, Dab or Dap; $R_{27}$ is Met, D-Met, Ala, Nle, Ile, Leu, Nva or Val; and $R_{29}$ is a D- or L-isomer of Cys, Abu, Asp, Glu, Orn, Lys, Dab or Dap.

* * * * *

UNITED STATES PATENT AND TRADEMARK OFFICE
CERTIFICATE OF CORRECTION

PATENT NO. : 5,043,322

DATED : August 27, 1991

INVENTOR(S) : Rivier, et al.

It is certified that error appears in the above-identified patent and that said Letters Patent is hereby corrected as shown below:

ABSTRACT: Line 10, change "N'Me." to --$N^a$Me,--. IN THE SPECIFICATION: Column 1, line 53, change "or" to --(C$\alpha$Me)--; line 54, delete "L(ame)"; line 54, change "(Name) to --($N^a$Me)--; Column 2, line 30, change "a bu" to --Abu--; line 45, change "Gln-Gly-$R_{34}$" to --Gln-Gly-Glu-$R_{34}$--; Column 6, line 64, change "$CH_2C_{12}$ to --$CH_2Cl_2$--; Column 12, line 15, after "Phe" and before "Ser", insert --Thr--; line 34, after "Ala$^{15}$," insert --D-Cys$^{25}$,--; line 38, after "Val-", insert --Leu--; Column 13, line 56, after "Arg-", insert --$R_{21}$-Leu-Leu- --; Column 14, line 53, change "Ser" to --Asn--; Column 16, line 57, change "553" to --1553--; IN THE CLAIMS: Column 18, line 65, before "-$R_{34}$", insert --Glu--; Column 19, line 26, after "is", insert --Orn.--; Column 20, line 1, before "(25-29)", insert --c--; line 2, delete "k".

Signed and Sealed this

Twelfth Day of January, 1993

Attest:

DOUGLAS B. COMER

Attesting Officer

Acting Commissioner of Patents and Trademarks